Figure 1:
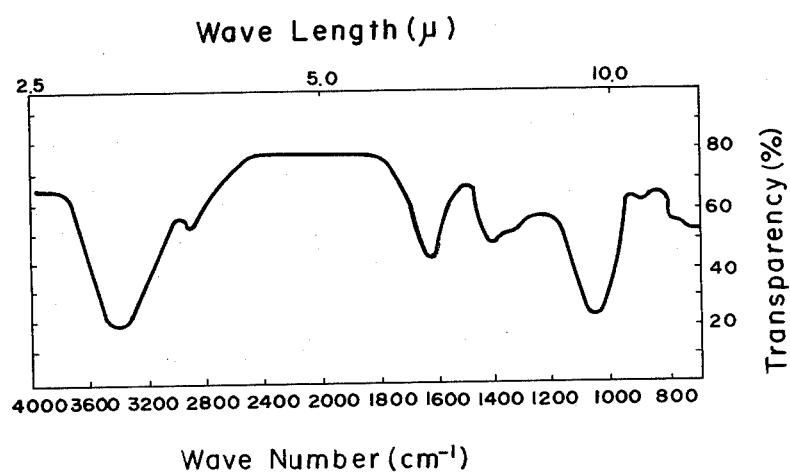

United States Patent [19]

Takayama et al.

[11] 4,230,800

[45] Oct. 28, 1980

[54] **PROCESS FOR PRODUCING A POLYSACCHARIDE USING *PSEUDOMONAS POLYSACCHAROGENES* M-30**

[75] Inventors: Toshihiro Takayama; Fujio Endo; Tsuneo Nozawa; Yoshiro Masuda; Motokuni Mori; Toshiji Kanayama, all of Ami, Japan

[73] Assignees: Mitsubishi Petrochemical Company Limited; Mitsubishi Yuka Pharmaceutical Co., Ltd., both of Tokyo, Japan

[21] Appl. No.: 920,142

[22] Filed: Jun. 29, 1978

[30] Foreign Application Priority Data

Nov. 8, 1977 [JP] Japan .................................. 52/133104

[51] Int. Cl.³ .................... C12P 19/04; C12R 1/38

[52] U.S. Cl. ...................................... 435/101; 435/247; 435/253; 435/874

[58] Field of Search ...................... 435/101, 247, 874; 536/1

[56] References Cited

U.S. PATENT DOCUMENTS

| | | | |
|---|---|---|---|
| 3,856,774 | 12/1979 | Hilzman | 435/101 |
| 3,878,045 | 4/1975 | Tannahill et al. | 435/101 |

*Primary Examiner*—Thomas G. Wiseman
*Attorney, Agent, or Firm*—Frishauf, Holtz, Goodman & Woodward

[57] ABSTRACT

New polysaccharide named M-30-C produced by cultivation of new strain *Pseudomonas polysaccharogenes* M-30 and having utility as hypocholesterol agents.

2 Claims, 6 Drawing Figures

PROCESS FOR PRODUCING A POLYSACCHARIDE USING *PSEUDOMONAS POLYSACCHAROGENES* M-30

This invention relates to a new polysaccharide, a process for producing the same and a pharmaceutical preparation containing the same. More particularly, it is concerned with a new polysaccharide named "M-30-C", a process for the production of the said polysaccharide which comprises cultivating a new strain named *Pseudomonas polysaccharogenes* M-30, as well as a composition for reduction in cholesterol which contains as an active ingredient the said polysaccharide.

For fermentative production of polysaccharides have been heretofore proposed various processes, most of which have utilized a medium containing as a main carbon source glucides. On the other hand, an attempt was made to employ as a carbon source such petrochemical products as normal paraffin, ethanol, propanol, ethylene glycol, an organic acid and the like, apart from the glucides (Japanese Patent Provisional Publication No. 18493/1973). However, such carbon sources have problems on solubility in water, supply and cost for fermentation materials and the like, without a satisfactory yield of a polysaccharide.

The present inventors have now paid a special attention to methanol, which has recently been marked as an inexpensive carbon source, and isolated many methanol-utilizable bacteria from soil samples collected in the Shimotsuma districts of Ibaraki-prefecture, Japan, on May 1, 1975 and screened them. As a result, it has been successfully accomplished to isolate a new strain belonging to the genus of Pseudomonas, which can produce a polysaccharide of being viscous when dissolved in water or hot water in a medium very easily and in a high yield, by cultivating in a medium containing a sole or major carbon source methanol. As a further result from our studies on the polysaccharides produced by the said new strain, it has been found that the so produced polysaccharide is a novel polysaccharide useful as a cholesterol reducing agent. Then, the present invention has been completed upon the above-mentioned findings.

Morphological properties of the new strain, *Pseudomonas polysaccharogenes* M-30 (frequently referred to as M-30 hereinafter), which may be employed in practising the present invention are summarized hereinbelow. This new strain has been deposited with Technical Research Institute of Microbial Industry, Agency of Industrial Science & Technology, Ministry of International Trade and Industry, Japan, and added to its collection of microorganisms under accession number 4054; this new strain has been deposited in American Type Culture Collection, U.S.A. under accession number ATCC Number 31414.

I. MORPHOLOGICAL CHARACTERISTICS

Observed a stationary cultured broth in a bouillon-methanol (0.5 v/v %) medium at 30° C. for 48 hours.
(1) Shape and size of cell: Bacilliform, 0.3–0.5×1.0–2.5μ
(2) Colony: Usually single, but frequently twin
(3) Motility: Motile with one flagellum
(4) Spore: None
(5) Gram stain: Negative
(6) Acid fasteners: Negative

II. GROWTH CHARACTERISTICS IN VARIOUS MEDIA (1) Bouillon culture: Grown
 (i) Bouillon liquid stationary culture (at 30° C. for 5 days): Growth-Abundant, Formation of film-None, Precipitate-Observed, Turbidity-Observed.
 (ii) Bouillon-agar slant culture (at 30° C. for 10 days): Growth-Abundant, Shape-Filamentary, Surface-Smooth, glossy, Peripheral-Wavy, Transparency-Opaque, Color tone-Orange.
 (iii) Bouillon-agar plate culture (at 30° C. for 21 days): Shape-Rather irregular, Peripheral-Wavy, Surface rising-Flat, Surface-Smooth.
 (iv) Bouillon-agar stab culture (at 30° C. for 7 days): Grown over surface and along upper stab.
(2) Bouillon-methanol (0.5 v/v %)-agar plate culture (at 30° C. for 30 days): Shape-Round, Peripheral-Wavy, Shape of surface rising-Flat, Surface-Smooth, Color tone-Deep orange
(3) Methanol synthetic liquid medium (0.5 g. of potassium nitrate, 1 g. of potassium dihydrogenphosphate, 0.5 g. of magnesium sulfate 7 hydrate, 10 mg. of ferrous sulfate 7 hydrate, 0.1 g. of yeast extract and methanol 1 v/v % dissolved in 1 l. of pure water and adjusted to pH 7.0) (at 30° C. for 5 days): Growth-Abundant, Precipitate-Observed, Turbidity-Observed, Formation of film-None

III. PHYSIOLOGICAL CHARACTERISTICS (1) Nitrate reduction: Positive
(2) Denitrification: Negative
(3) MR (Methyl Red) test: Negative
(4) VP (Voges-Proskauer) test: Negative
(5) Indole formation: Negative
(6) Hydrogen sulfide formation: Negative
(7) Starch hydrolysis: Negative
(8) Utilization of inorganic nitrogen sources: Only ammonium salts and nitrates utilized as nitrogen source
(9) Pigment formation: None
(10) Urease: Positive
(11) Oxidase: Positive
(12) Catalase: Positive
(13) Oxygen requirement: Aerobic
(14) Gelatin liquefaction: Negative (15) Litmus milk: Red-colored, peptonized
(16) Growth temperature: 10°–37° C., Optimum growth temperature 26°–31° C.
(17) Growth pH: pH 5–10, Optimum pH 6–8
(18) Utilization of methylamine: None
(19) Production of acid (gas) from sugars: Arabinose, adonitol, inositol, galactose, xylose, glucose, saccharose, dulcitol, sorbitol, trehalose, maltose, mannitol, mannose, lactose, rhamnose, raffinose, fructose, starch and glycerol: All negative (all negative)
(20) Utilization of carbon sources:
 (i) Utilization of sugars: Arabinose, inositol, galactose, xylose, saccharose, sorbitol, trehalose, maltose, mannitol, mannose, lactose, rhamnose, raffinose, fructose, starch, dextrin, inulin, α-methylglucoside, ribose, sorbose, fucose, cellobiose, melebiose and glycerol: All negative; Gluose: Positive
 (ii) Utilization of alcohols: Methanol: Positive; Ethanol, n-propanol, isopropanol, n-butanol, n-amylalcohol, isoamylalcohol, 1,2-propanediol, 1,3-butanediol, 1,4-butanediol, 2,3-butanediol, 1,5-pentanediol, 1,6-hexanediol, 2,5-hexanediol, ethylene glycol, diethylene glycol, 4-methylcyclohexane: All negative (iii) Utilization of organic acids: Formic acid, acetic acid, fumaric acid, citric acid, lactic acid, pyruvic acid, isocitric acid, ketoglutaric acid, succinic acid, malic acid, oxalacetic acid, glycolic acid, glyoxylic acid, glyconic acid: All negative Searching for any proper genus upon the aforesaid morphological characteristics by making reference to "Bergey's Manual of Determinative Bacteriology", 8th Ed., R. E. Buchanon & N. E. Gibbons, Williams & Wilkins Co., (1974), it becomes clear that the present strain belongs to the genus of Pseudomonas, as it is gram-negative, baciliform, motile with flagellum and aerobic and also it may oxidatively decompose glucose. Although comparison of this strain with species class of the above genus is made, there can not be found any description sufficient to identify this strain strictly.

Moreover, methanol-utilizable bacteria generally have color tones of predominantly pink or like color, in their colonies, whereas the present strain shows an orange color tone in its colony and no utilization of methane and ethanol and does produce a significant amount of a polysaccharide from methanol, together with different productivity of acids from various carbon sources and utilization. It is, therefore, considered that the present strain differs from such known species as *Pseudomonas methanica, Pseudomonas methylotropha, Pseudomonas rosea, Pseudomonas methylooxidans* M-59, *Pseudomonas aerogenes, Pseudomonas insueta,* Pseudomonas PRL-W4, Pseudomonas AM-1, Pseudomonas M-27, Pseudomonas C and the like.

On the other hand, comparing with known strains capable of utilizing methanol and producing polysaccharides, the present strain differs from *Methylomonas mucosa* and *Methanomonas polysaccharogenes* in utilization of glucose and also from Pseudomonas SP. S46-B1 in colony tone and production of acids from various sugars.

And, in comparison of M-30 with a relatively similar well-known species, *Methanomonas polysaccharogenes* 26, M-30 clearly differs from the latter mainly in Litmus milk reaction and hydrogen sulfide production and then is to be considered as belonging to a different species.

From the foregoing, the present strain can be reasonably considered as a novel species belonging to the genus Pseudomonas and has been, accordingly, named *Pseudomonas polysaccharogenes* M-30 as previously mentioned.

In practising the fermentative process of this invention, cultivation is conducted under aerobic condition in a medium containing methanol as a sole or major carbon source.

An amount of the methanol to be incorporated into a medium is desirably of not more than 4 v/v % to a medium. In case where methanol is continuously fed to a medium, it is desirable to maintain the methanol content in a medium at not more than 1 v/v %.

As inorganic nitrogen sources may be utilized ammonium nitrate, potassium nitrate, ammonium sulfate and the like and yeast extract, peptone and the like may be used as natural nitrogen sources. Other inorganic components than the nitrogen sources, which may be utilized, includes, for example, dipotassium hydrogenphosphate, potassium dihydrogenphosphate, magnesium sulfate, ferrous sulfate, calcium chloride, magnesium sulfate, manganese sulfate, sodium chloride and so on.

Vitamins are not particularly required, but biotin, thiamines, yeast extract, corn steep liquor and the like may be added, if necessary.

Cultivation may be usually and preferably carried out under aerobic condition. For instance, cultivation is satisfactorily conducted at a cultivation temperature of 10°–37° C., preferably 28°–32° C., under shaking or aerated agitation. The pH of cultivation is in a range of 5–10, preferably 6–8, most preferably 6.5–7.5 and a cultivation period may be sufficiently in 24 hours or more with 48–72 hours being preferable.

After completion of the cultivation, a cultured broth is diluted to a 10–20 times volume and mycelia and other solid materials are removed by a continuous centrifugation, for example, at $15000 \times g$. with a treating rate of 20 l./hr. or by a batchwise centrifugation, for example, at $10000 \times g$. for 60 minutes. Then, an organic solvent such as methanol, ethanol or acetone in an about twice volume or a quarternary ammonium salt is added to the cetrifuged broth for fractional precipitation to produce a white fibrous crude polysaccharide.

The crude polysaccharide thus produced is dissolved in an about 5–15 times volume of water, resulting solution is subjected to deproteinization, for example, heating at 70°–100° C., treating with a mixture of chloroform and amyl alcohol (e.g., 3:2) or treating with trichloroacetic acid, a continuous or batchwise centrifugation in the same manner as in the above crude polysaccharide for removal of proteins and an approximately twice volume of methanol, ethanol or acetone is added to the resulting supernatant. The so separated precipitate is thoroughly washed with ether or ethanol, again dissolved in 5–15 times volume of water and demineralized by dialysis against a running water, treatment with an ion exchanger or gel filtration followed by freeze-drying to yield a purified polysaccharide in a white spongy state.

The physico-chemical properties of the polysaccharide thus obtained are as defined below.

(a) Optical rotation: $[\alpha]_D^{20} = +48.4° \pm 3.3°$ (0.1 w/v % aqueous solution)

(b) Weight average molecular weight: $2.0 \times 10^5 - 2.0 \times 10^6$ The molecular weight varies depending upon the fermentation period of time.

(c) Elemental analysis: C, 37.7% ± 3.0%; H, 5.8% ± 0.5%

(d) Color reaction: Positive in anthrone reaction and phenol-sulfuric acid reaction (e) Determination of basicity, acidity or neutrality: Acidic polysaccharide (f) Infrared absorption spectrum: Characteristic absorption bands (cm$^{-1}$) at 3450(S), 2940(M), 1620(M), 1400(M), 1040(S) and 890(W)

(g) Solubility: Soluble in water, 1 N hydrochloric acid, 1 N sulfuric acid and 1 N aqueous ammonia. Insoluble in ethanol, ether, acetone, chloroform and dimethyl sulfoxide.

(h) Viscosity: 1000–3000 cps measured on its 1.0 w/v % aqueous solution at 20° C. by means of BL-type viscometer (manufactured by Tokyo Keiki K.K., Japan)

(i) Sugar units: Spots of glucose and mannose on paper chromatography after hydrolysis and sugar unit ratio of glucose to mannose of 3:2 by gas chromatography (j) Color and Shape: White and amorphous as such and colorless in its aqueous solution.

It can be reasonably concluded from the above-recited properties that the polysaccharide isolated from a cultured broth of the new strain *Pseudomonas polysac-*

*charogenes* M-30 is a novel substance and the present inventors have then given a name of "polysaccharide M-30-C" thereto.

The polysaccharide M-30-C shows a high viscosity in its aqueous solution and further no reduced viscosity even in the presence of a salt, e.g., KCl, $MgCl_2$, $AlCl_3$, $(NH_4)_2SO_4$ or NaCl. The viscosity of its aqueous solution is not so much varied upon changes in its pH values. Therefore, the polysaccharide M-30-C is valuable as food additives, carriers for medicines and cosmetics or industrial chemicals, e.g., drilling lubricants.

In medicinal applications of the polysaccharide M-30-C, it has been noted that the polysaccharide is useful as a hypocholesterol agent upon its cholesterol-reducing activity.

Hypocholesterol effects of the polysaccharide M-30-C are more fully explained hereinbelow with various experimental results.

$LD_{50}$ value of the polysaccharide M-30-C is not less than 5 g./kg. in ICR-JCL strain male and female mice and Wistar strain male and female rats when administered orally, while $ED_{50}$ value of inhibitory effect on increase in blood cholesterol level is not more than 5 mg./kg. in case of hyperlipemia induced by Triton. Thus, the safety zone ($LD_{50}/ED_{50}$) of the polysaccharide is as high as 1000 times or more. As to subacute toxicity over one-month administration, no abnormalities in all of body weight, blood and organs have been observed with a continuous administration of 500 mg./kg./day and the maximum safety dose is 500 mg./kg. with regard to subacute toxicity. The polysaccharide does, therefore, show a high safety as a drug and is then applicable as a medicine for improvement in lipid metabolism and prevention of atherogenesis.

The polysaccharide may be administered via oral, intravenous, sublingual, intramusclar or intrarectal route, but oral administration is most preferable, usually in a single dose of 10–1000 mg. once to six times daily for adults. In some cases, the polysaccharide may be given after suitably cleaved or sulfated.

The polysaccharide M-30-C can be given as a drug for improved lipid metabolism to improve or prevent atherosclerosis, myocardial infarction angina pectoris, cerebro-malacia, cerebral hemorrhage, hypertension or hypercholesteremia associated with diabetes.

For oral administration, there may be commonly employed such preparations as capsules, tablets or granules and, in some cases, powders, syrups or aqueous solutions may be also applied.

Moreover, the polysaccharide M-30-C has additional characteristic advantages in that it exerts its effect in a lower effective dose as compared with known hypocholesterol agents, that it has a wide safety range and that it does develop no hepatotoxicity which is typical of side effects liable to be accompanied.

This invention is more fully explained by way of the following examples.

EXAMPLE 1

One gram of potassium dihydrogenphosphate, 1 g. of potassium nitrate, 0.5 g. of magnesium sulfate 7 hydrate, 0.5 g. of potassium chloride, 0.1 g. of yeast extract, 10 mg. of ferrous sulfate 7 hydrate, 2 mg. of calcium chloride dihydrate, 2 mg. of sodium chloride and 32 g. of methanol were dissolved in 1 l of pure water to make up a medium. Seven liters of this medium were prepared, adjusted its pH to 7.0 and poured into a 10 l-volume jar fermenter, which was then sterilized at 120° C. for 10 minutes.

*Pseudomonas polysaccharogenes* M-30, which was seed-cultured on a medium of the same composition as above in a Sakaguchi flask, was inoculated to the above-mentioned jar fermenter and cultivation was then conducted at a cultivation temperature of 30° C. and an aeration of 0.5 VVM.

After cultivation for 72 hours, water was added to a cultured broth to make up 100 l. and mycelia were removed by a continuous centrifugation under conditions of 20,000 rpm and 7 l./hr. by means of a sharpless centrifuge. Thereafter, the centrifuged supernatant was heated to 80° C. for 15 minutes and adjusted its pH to 3.5–4.5 with hydrochloric acid to make proteins precipitated at an isoelectric point, which were then removed by centrifugation. The centrifuged supernatant was adjusted to pH 7.0, concentrated to 25 l., treated with chloroform-amyl alcohol (3:2) for deproteinization and then 50 l. of acetone were added, thereby yielding a viscous substance in the form of a fibrous mass. The substance was filtered off, thoroughly washed with ether and then ethanol, dissolved again in water and dialyzed. Again, a twice volume of acetone was added to separate a polysaccharide. The polysaccharide was dissolved in 2 l. of pure water followed by freeze-drying to afford 98 g. of the purified polysaccharide M-30-C. Its productivity was 14.0 g. per liter of the cultured broth.

Figure 3:
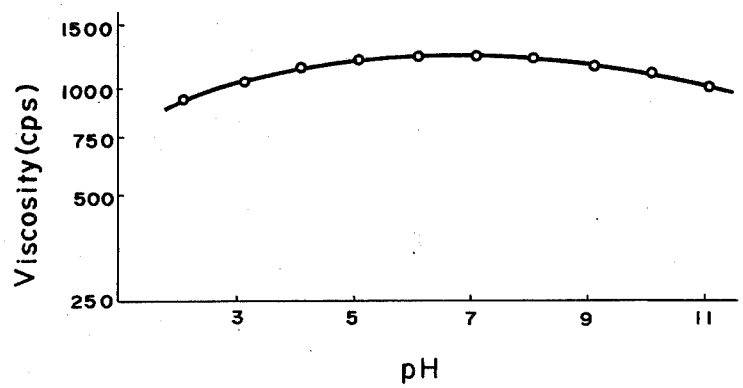

Physico-chemical properties of the polysaccharide thus produced are as recited below.
(a) Optical rotation: $[\alpha]_D^{20} = \pm 48.4°$ (0.1 w/v % aqueous solution)
(b) Average molecular weight: 1,800,000 by gel filtration and 1,200,000 by light scattering
(c) Elemental analysis: C, 37.7%; H, 5.8%.
(d) Color reaction: Positive in anthrone reaction and phenolsulfuric acid reaction
(e) Determination of basicity, acidity or neutrality: Addition of cetyl trimethylammonium bromide or cetyl pyridinium chloride to an aqueous solution of the polysaccharide M-30-C gives white precipitates. The polysaccharide M-30-C is, therefore, an acidic polysaccharide.
(f) Infrared absorption spectrum: Characteristic absorption bands are expressed by a wave number ($cm^{-1}$) as shown below. 3450(S), 2940(M), 1620(M), 1400(M), 1040(S) and 890(W) wherein S shows a strong absorption, M a moderate absorption and W a weak absorption. Also, see FIG. 1.
(g) Solubility: Soluble in water, 1 N hydrochloric acid, 1 N sulfuric acid and 1 N aqueous ammonia. Insoluble in ethanol, ether, acetone, chloroform and dimethylsulfoxide.
(h) Viscosity: 1000–3000 cps measured in a 1.0 w/v % aqueous solution of the polysaccharide M-30-C under conditions of 20° C. and 60 rpm by means of BL-type viscometer (manufactured by Tokyo Keiki K.K., Japan)
(i) Change in viscosity of aqueous solution by pH: Within a pH range of 2–11, a somewhat higher viscosity is observed around neutral pH, the viscosity at pH 2 is 930 cps, that at pH 7 is 1250 cps and that at pH 11 is 1100 cps, using BL-type viscometer with HM-3 adapter for a minor amount and conditions for determination of 20° C., 0.25 w/v % aqueous solution and 6 rpm. Also, see FIG. 3.

Figure 4:
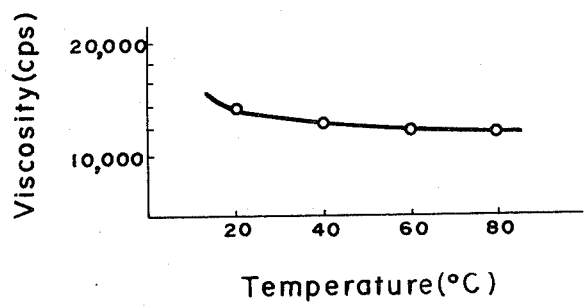

(j) Change in viscosity of aqueous solution by temperature: Within 20°–80° C., the higher a temperature is, the somewhat lower a viscosity becomes. The viscosity at 20° C. is 13,500 cps and that at 80° C. is 11,100 cps, using the same viscmeter and concentration as in the above (h) except for a rotary speed of 6 rpm. Also, see FIG. 4.

Figure 5:
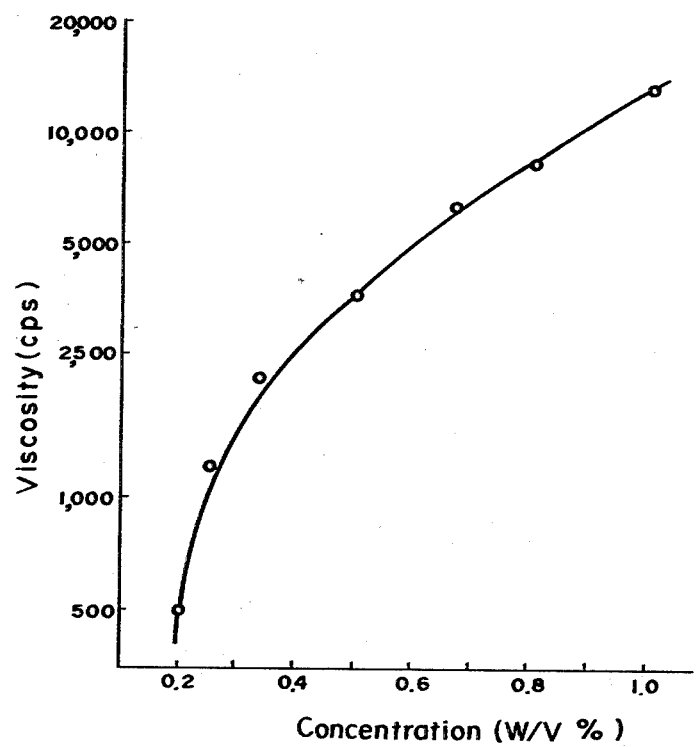

(k) Change in viscosity of aqueous solution by concentration: Concentrations of an aqueous solution of the polysaccharide M-30-C are changed over a range of 0.2 w/v % to 1.0 w/v %. The higher a concentration is, the higher a viscosity becomes, as clearly shown by 500 cps at 0.2% and 13,500 cps at 1.0%, using a temperature of 20° C. and the same viscometer and conditions (rpm) as in the above (j). Also, see FIG. 5.

(m) Change in viscosity of aqueous solution by salt: No reduction in the viscosity of an aqueous solution of the polysaccharide is observed in a 5 w/v % aqueous solution of potassium chloride, magnesium chloride, aluminum chloride and ammonium sulfate or a saturated aqueous solution of sodium chloride.

(n) Sugar units: The polysaccharide M-30-C is hydrolyzed with 2 N sulfuric acid in a sealed tube at 100° C. for 9 hours. The reaction product is treated with barium hydroxide to remove the sulfuric acid and then passed through a column of an ion exchange resin Dowex 50 (H form) (available from Dow Chemical Co., U.S.A.) to remove excess barium ions and fine particles of barium sulfate. The effluent is concentrated under reduced pressure. The concentrate is subjected to paper chromatography using butanol: acetic acid: water (4:1:5) as a developing solvent to give spots of glucose and mannose. The concentrate is further evaporated to dryness and converted to the corresponding trimethylsilyl derivative. Its gas chromatography shows the ratio of glucose to mannose of 3:2.

(o) Color and shape: The polysaccharide M-30-C is white and amorphous, its aqueous solution being colorless.

(p) Taste and odor: The polysaccharide M-30-C and its aqueous solution are tasteless and odorless.

(q) Comparison of viscosity: The polysaccharide M-30-C has a higher viscosity, as compared with xanthane gum. Conditions for determination are 20° C., an 1.0 w/v % solution, 60 rpm and the same viscometer as in the above (h). The polysaccharide M-30-C has 2100 cps and xanthane gum has 1000 cps.

Figure 2:
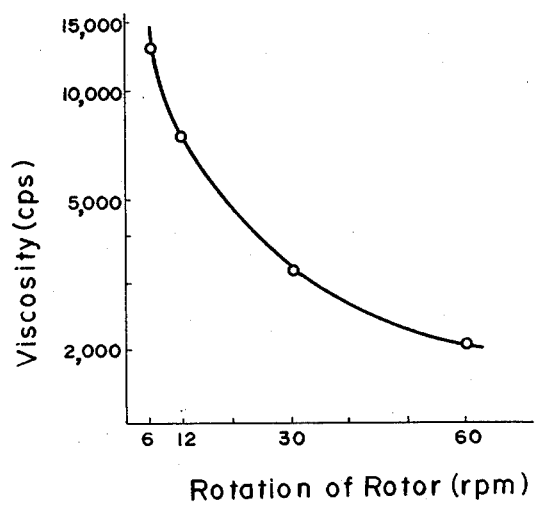

(r) Thixotropic property: The polysaccharide M-30-C shows a thixotropic property in its aqueous solution (See "Rheology", Kakutaro Nakagawa et al. pages 97–98, published as one of Iwanami Complete Books). The relationship between rotation numbers in a viscometer and viscosities is shown in FIG. 2. The same viscometer and conditions as in the above (h) are employed here.

(s) Stringing: The polysaccharide M-30-C shows little stringy nature in its aqueous solution.

Figure 6:
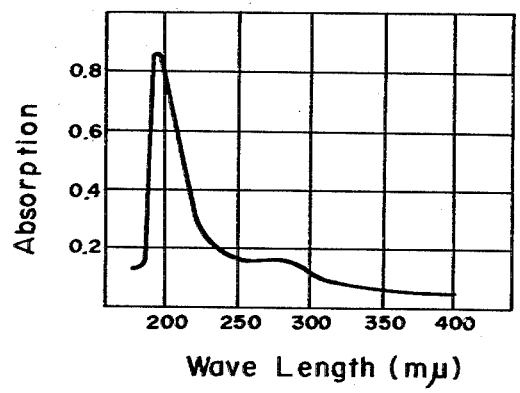

(t) Ultraviolet absorption spectrum: Weak absorption observed at around 280 mµ as shown in FIG. 6.

(u) Melting point: Indefinite, decomposes with heating, becoming carbonized state.

EXAMPLE 2

Cultivation was conducted in the same manner as in the above Example 1 to produce a cultured broth containing the polysaccharide M-30-C. The cultured broth was diluted with water-methanol (1:1) to 100 l. and heated to 80° C. for 15 minutes. Then, mycelia were removed by continuous centrifugation under condition of 7 l./hr. by means of a sharpless centrifuge. The centrifuged supernatant was adjusted its pH to 3.5–4.5 with hydrochloric acid to make proteins precipitated at isoelectric point, which were removed by centrifugation. The centrifuged supernatant was adjusted its pH to 7.0 and an aqueous solution of calcium chloride was added thereto in a sufficient amount to be a concentration of 0.02 w/v %. Further centrifugation gave a paste-like polysaccharide. This product was treated in 20 l. of methanol with thorough stirring to remove salts, filtered and the methanol was removed to leave a polysaccharide as a paste. It was then dissolved in 2 l. of pure water and freeze-dried to afford 84 g. of the purified polysaccharide M-30-C. Its productivity was 12.0 g. per liter of the cultured broth.

In order to demonstrate pharmacological properties of the present polysaccharide M-30-C, there are given the following Experiments.

EXPERIMENT 1

Male ICR-JCL strain mice, each group consisting of 10 animals, were used and given intravenously with Triton 800 mg./kg. After 20–24 hours from the administration, a peak level of blood lipid was given and thereafter hyperlipemia was maintained over 24 hours or longer in host animals. Thus, there were prepared test animals with hyperlipemia induced by Triton.

The test sample (M-30-C) was dissolved in distilled water and orally administered to animals twice, namely, immediately after Triton administration and after 20–24 hours. After 24 hours from the above final administration, a serum cholesterol level was determined.

EXPERIMENT 2

Male ICR-JCL strain mice, each group consisting of 6 animals, were used and given intravenously with Streptozotocin 200 mg./kg. After 7 days from the administration, hyperlipemia was maintained over 14 days or longer to prepare test animals with endogenous hyperlipemia induced by Streptozotocin.

The test sample (M-30-C) was dissolved in distilled water and orally administered to animals at a single daily dose of 50 mg./kg. for 5 days after 7 days from the Streptozotocin administration. After 24 hours from the above final administration, a serum cholesterol level was determined.

EXPERIMENT 3

Male Wistar strain rats were used, each group consisting of 10 animals, in the 3 Groups as defined above. "Normal Animal Groups" (Normal Control) contained host animals given with a conventional powder feed. "Cholesterol Control Groups" (Positive Control) contained host animals given with a feed comprising the conventional powder feed, cholesterol 0.5% and bilic acid 0.5%. "M-30-C-given Groups" contained host animals given with a feed comprising the feed in the above cholesterol control groups and the test sample (M-30-C) prepared to supply a daily dose of 50 mg. of the sample per kg. Plasma cholesterol levels in all groups were raised at the same time, the feed being given in a daily amount of 10 g. per 100 g. of body weight. After feeding for 14 days, a serum cholesterol level was determined.

In these Experiments 1-3, a commercially available hypocholesterol agent (CPIB) was similarly tested for comparative purposes.

The results from the Experiments 1-3 are summarized in the following Table 1.

65.9% atherosclerosis ratio is seen in dorsal aorta of the Positive Control, whereas approximate 30–40% of inhibition of atherosclerosis is observed in the M-30-C-given Group. Further, it is believed that a lowering action on serum lipids by the polysaccharide M-30-C is

TABLE 1

Effects of M-30-C on serum cholesterol*

|  | Normal Control | Positive Control | M-30-C-given Group | | | Clofibrate-given** Group | |
|---|---|---|---|---|---|---|---|
|  |  |  | 1 mg/kg/ dose unit | 5 mg/kg/ dose unit | 50 mg/kg/ day | 100 mg/kg/ dose unit | 300 mg/kg/ dose unit or day |
| Experiment 1 Hyperlipemia induced by Triton | 109.0 ± 9.0 | 401.2 ± 18.0 | 299.6 ± 24.9 | 247.1 ± 21.7 | — | 396.0 ± 23.0 | 191.9 ± 28.8 |
| Experiment 2 Hyperlipemia induced by Streptozotocin | 128.2 ± 10.3 | 200.0 ± 10.3 | — | — | 163.1 ± 14.4 | — | 177.4 ± 10.3 |
| Experiment 3 Hyperlipemia induced by high-cholesterol feed | 72.9 ± 3.0 | 250.2 ± 9.9 | — | — | 191.1 ± 16.7 | — | 384.2 ± 21.7 |

*mg/dl; expressed as mean ± standard error
**Commercially available hypocholester l agent having the structure

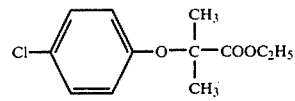

EXPERIMENT 4

Male Newzealand-White strain rabbits were used, each group consisting of 10–14 animals.

Animals given with a conventional pellet chow were classified as "Normal Group" (Normal Control), those given with a feed of the conventional feed and cholesterol 0.67% as "Cholesterol Control Group" (Positive Control) and those given with a feed of the feed in the Positive Control and test sample (M-30-C) as "Test sample-given Group". Plasma cholesterol levels in all groups were raised at the same time with a daily feed supply of 40 g./kg. of body weight for 20 weeks.

During this period was determined a serum lipid level. After 20 weeks, all animals were bled out and dorsal aorta was excised and then effects on atherosclerosis were examined.

The results are summarized in the following Table 2.

It can be seen from the Table that the polysaccharide M-30-C does significantly inhibit increase in serum lipids (total and free cholesterol, triglyceride, phospholipid, lipoprotein, free fatty acid); more specifically, due to inhibitory effects on absorption and biosynthesis of cholesterol.

In view of only the above fact that appearance of experimental atherosclerosis can be significantly inhibited, the polysaccharide M-30-C may be considered applicable as practical serum lipid reducing agents and atherosclerosis-preventing agents.

TABLE 2

|  | Weeks | Normal Control | Positive Control | M-30-C-given Group | | Clofibrate-given Group |
|---|---|---|---|---|---|---|
|  |  |  |  | 30 mg/kg/day | 100 mg/kg/day | 100 mg/kg/day |
| Cholesterol (mg/dl) | 6 | 45.5 ± 2.7*** | 1475.4 ± 153.2 | 1297.9 ± 174.1 | 947.9 ± 81.5** | 916.5 ± 218.2* |
|  | 12 | 58.5 ± 4.6*** | 2003.8 ± 421.4 | 1130.0 ± 142.1* | 917.9 ± 119.2** | 1466.8 ± 182.5 |
|  | 18 | 41.6 ± 4.7*** | 1772.1 ± 517.3 | 909.2 ± 99.0* | 736.5 ± 46.1** | 1075.7 ± 59.3 |
| Triglyceride (mg/dl) | 6 | 54.3 ± 6.2*** | 942.6 ± 149.3 | 876.4 ± 239.1 | 293.6 ± 62.5** | 326.0 ± 180.3* |
|  | 12 | 75.6 ± 6.6*** | 721.7 ± 390.0 | 378.1 ± 167.1 | 258.0 ± 77.6** | 343.1 ± 55.3* |
|  | 18 | 97.0 ± 31.6*** | 655.1 ± 187.5 | 455.5 ± 133.6 | 187.8 ± 50.2** | 366.9 ± 112.1 |
| Atherosclerosis Ratio | 20 | 0 | 65.9 ± 7.0 | 45.1 ± 9.4 | 41.5 ± 8.4* | 58.1 ± 7.9 |
| Inhibition percent (%) | 20 |  | 0 | 31.6 | 37.0 | 11.8 |

Atherosclerosis Ratio (%) = $\frac{\text{Atherosclerosis aria}}{\text{Total aria (Aorta)}} \times 100$

*t < 0.05,
**t < 0.01,
***t < 0.001

What is claimed is:

1. A process for the production of a polysaccharide which comprises cultivating a microorganism having the identifying characteristics of *Pseudomonas polysaccharogenes* M-30 in a medium containing methanol as a sole or major carbon source and isolating a polysaccharide from a cultured broth.

2. A process according to claim 1 wherein said cultivation is conducted in a medium of pH 6.5–7.5 at 28°–30° C. for 48–72 hours, solid materials are removed from a cultured broth, a crude polysaccharide is precipitated and separated with a solvent for precipitation and then said polysaccharide is purified by deproteinization.

* * * * *